United States Patent [19]

Cooper et al.

[11] Patent Number: 5,115,307
[45] Date of Patent: May 19, 1992

[54] ELECTRONIC VIDEO DENTAL CAMERA

[75] Inventors: David H. Cooper, Saratoga; Charles S. Bush, Los Gatos, both of Calif.

[73] Assignee: Fuji Optical Systems, Los Gatos, Calif.

[21] Appl. No.: 388,666

[22] Filed: Aug. 2, 1989

Related U.S. Application Data

[60] Division of Ser. No. 149,521, Jan. 28, 1988, Pat. No. 5,016,098, which is a continuation-in-part of Ser. No. 22,177, Mar. 5, 1987, Pat. No. 4,727,416.

[51] Int. Cl.⁵ .......................... A61B 1/04; A61B 1/06; A61B 1/24
[52] U.S. Cl. .................................... 358/98; 128/633; 433/29
[58] Field of Search ................... 358/98; 433/29, 31, 433/114; 128/633

[56] References Cited

U.S. PATENT DOCUMENTS

| | | |
|---|---|---|
| 3,382,781 | 5/1968 | Hamilton |
| 3,622,785 | 11/1971 | Irwin |
| 3,884,222 | 5/1975 | Moore |
| 4,260,376 | 4/1981 | Litel et al. |
| 4,369,768 | 1/1983 | Vukovic |
| 4,468,197 | 8/1984 | Provost |
| 4,479,499 | 10/1984 | Alfano |
| 4,522,196 | 6/1985 | Cunningham et al. |
| 4,575,805 | 3/1986 | Moermann et al. |
| 4,593,699 | 6/1986 | Poncy et al. |
| 4,601,284 | 7/1986 | Arakawa |
| 4,621,618 | 11/1986 | Omagari |
| 4,629,425 | 12/1986 | Detsch |
| 4,638,353 | 1/1987 | Nagasaki et al. |
| 4,667,229 | 5/1987 | Cooper et al. |
| 4,684,018 | 8/1987 | Jarund |
| 4,759,347 | 7/1988 | Ando |
| 4,836,206 | 6/1989 | Maxwell ............................ 128/633 |
| 4,928,691 | 5/1990 | Nicholson ........................ 128/633 |
| 5,007,837 | 4/1991 | Werly ............................... 433/29 |
| 5,016,098 | 5/1991 | Cooper ............................. 358/98 |
| 5,049,070 | 9/1991 | Ademovic ......................... 358/98 |
| 5,051,823 | 9/1991 | Cooper ............................. 358/98 |
| 5,052,924 | 10/1991 | Berg ................................. 433/29 |

FOREIGN PATENT DOCUMENTS

| | | |
|---|---|---|
| 0122537 | 10/1984 | European Pat. Off. |
| 0184778A3 | 6/1986 | European Pat. Off. |
| 2208902 | 8/1973 | Fed. Rep. of Germany |
| 3045162A1 | 1/1982 | Fed. Rep. of Germany |
| 922944 | 4/1963 | United Kingdom |

Primary Examiner—Howard W. Britton
Attorney, Agent, or Firm—Steven F. Caserza

[57] ABSTRACT

An electronic video dental camera is provided which overcomes the disadvantages of both prior art dental mirrors, endoscopes, and video endoscopes. The electronic video dental camera is readily manipulated by dentists who are familiar with the manipulation of dental mirrors. Such an electronic video dental camera includes a handle to be held the user, and a camera head located at the distal end of the handle, with the camera head being formed at an angle to the handle, as in prior art dental mirrors. One embodiment includes provision for the flow of a selected fluid in order to defog and/or clean the camera lens. In one embodiment, the camera head includes light sources for illuminating the area to be viewed. In one embodiment, the handle of the dental camera includes means for transporting all appropriate signals and fluids to and from the camera head, and, if desired, valves and switching means located on the handle for controlling such communication to the camera head. One embodiment includes a dental camera head which allows a number of attachments to be used, such as a telephoto lens, wide angle lens, relay lens, and transillumination devices. In an alternative embodiment, the dental camera is attached to another dental instrument, such as a dentist's drill, thereby allowing video monitoring of the task being performed. In another embodiment, the dental camera is formed as an integral part of the dental instrument.

16 Claims, 9 Drawing Sheets 5,115,307

ELECTRONIC VIDEO DENTAL CAMERA

This is a divisional of application Ser. No. 07/149,521 filed Jan. 28, 1988, now U.S. Pat. No. 5,016,098, which in turn is a continuation-in-part of U.S. Ser. No. 022,177 filed Mar. 5, 1987, now U.S. Pat. No. 4,727,416, both of which are assigned to Fuji Optical Systems, Inc., the assignee of this application.

BACKGROUND OF THE INVENTION

This invention is an electronic video dental camera having a handle and head for use in placement in a dental patient's mouth, and allowing areas within the mouth be displayed via a video signal.

For years, dentists have used dental mirrors for insertion in a dental patients' mouth for reflecting images of areas within the patients' mouth for viewing by the dentist. This technique works, although it has several disadvantages. First, it is often difficult to hold the dental mirror in an appropriate position in order to reflect the desired image. Secondly, it is more difficult to ensure that proper lighting is available to the area within the mouth to be reflected by the dental mirror. An even greater disadvantage is that it is very difficult to use such prior art dental mirrors in a situation where a dentist wishes to discuss certain regions within the mouth with other people, be it the patient, colleagues, dental assistants, or students in a teaching institution.

Electronic video endoscopes have been used in recent years, for example as is described in U.S. patent application Ser. No. 611,684 filed May 18, 1984 on an invention of Cooper et al, which is hereby incorporated by reference. Such prior art video endoscopes use either fiber optics or a miniature camera, such a charge coupled device (CCD), in order to transport an image to a monitor. Such prior art video endoscopes come in a variety of sizes, but are typically rather small and tubular in nature in order that they maybe easily inserted within a body cavity or surgical opening. Certain prior art endoscopes include a light source located at their end in order to ensure proper lighting is available for illumination of the area of the desired image.

However, such prior art video endoscopes were not specifically designed for use in dental applications and are rather clumsy in such applications. As one example, it is very difficult, if not impossible, to properly view the lingual aspects of the teeth using such prior art video endoscopes, due to their tubular shape.

SUMMARY OF THE INVENTION

In accordance with the teachings of this invention, an electronic video dental camera is provided which overcomes the disadvantages of both prior art dental mirrors, endoscopes, and video endoscopes. In accordance with the teachings of this invention, an electronic video dental camera is provided having a general shape of prior art dental mirrors, thereby being readily manipulated by dentists who are universally familiar with the manipulation of prior art dental mirrors. Such an electronic video dental camera includes a handle to be held the user, and a camera head located at the distal end of the handle, with the camera head being formed at an angle to the handle, as in prior art dental mirrors. In one embodiment, means are provided to cause, as desired, the flow of a selected fluid over the camera lens in order to defog and/or clean the camera lens, thereby allowing proper viewing. In one embodiment, the camera head also includes light sources for properly illuminating the area to be viewed. As a feature of one embodiment of this invention, the handle of the dental camera includes means for transporting all appropriate signals and fluids to and from the camera head, and, if desired, valves and switching means located on the handle for controlling such communication to the camera head.

In one embodiment of this invention, the handle is uniquely designed to include electronics, such as video amplifiers and imaging device driver circuitry, thereby eliminating the need to include this circuitry in the camera head itself. In an alternative embodiment of this invention, elements of this electronic circuitry is located in the cable, or connectors, or in the video processor unit itself.

One embodiment includes a dental camera head which allows a number of attachments to be used, such as a telephoto lens, wide angle lens, relay lens, and transillumination devices. In an alternative embodiment of this invention, the dental camera is attached to another dental instrument, such as a dentist's drill, thereby allowing video monitoring of the task being performed by the dentist. In yet another embodiment of this invention, the dental camera is formed as an integral part of the dental instrument, such as a dental drill.

DETAILED DESCRIPTION OF THE INVENTION

Figure 1:
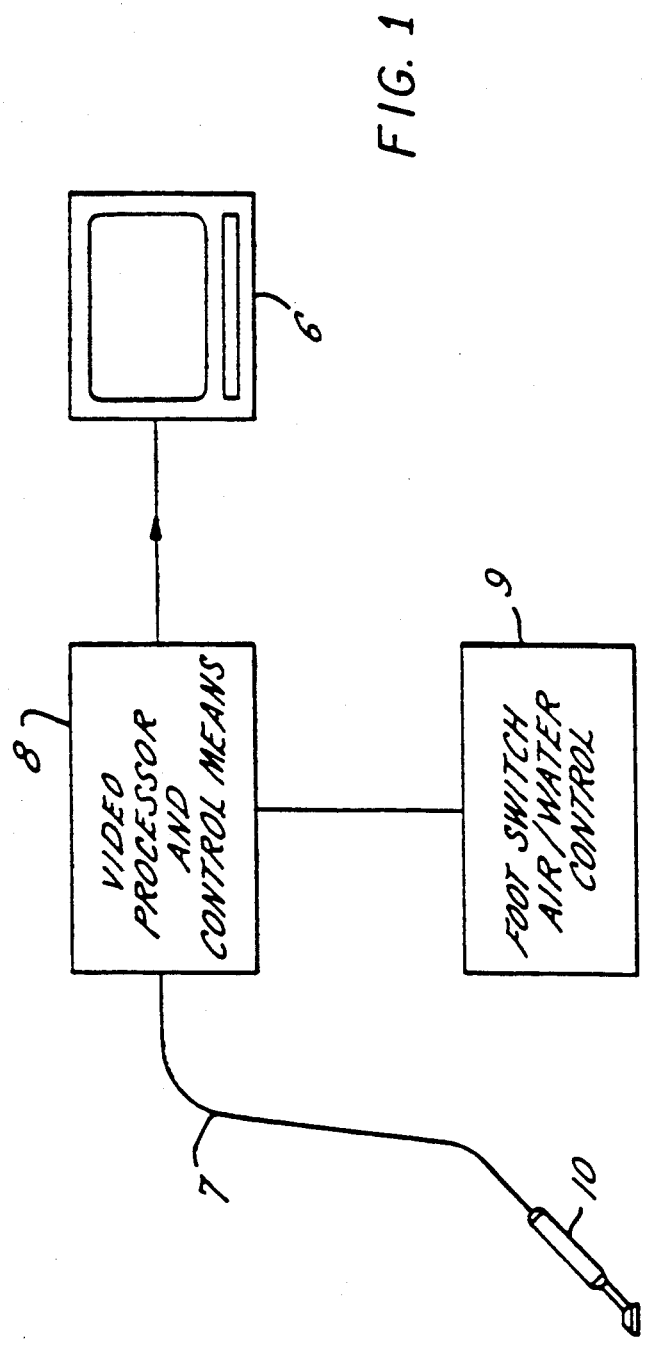
FIG. 1 is a diagram depicting the use of an electronic video dental camera system constructed in accordance with the teachings of this invention.

FIG. 1 shows the use of a dental camera 10 constructed in accordance with the teachings of this invention. Video processor and control means 8 serves to provide power, light and, if desired, fluid and other appropriate signals via cable 7 to dental camera 10. Video processor and control means 8 provides a video signal to video monitor 6 in order that users may view a location within a patient's mouth by way of dental camera 10. If desired, foot switch 9 is used to provide a signal to video processor and control means 8 indicating when air and/or fluids are to be sent by video processor and control means 8 to dental camera 10.

Figure 2:
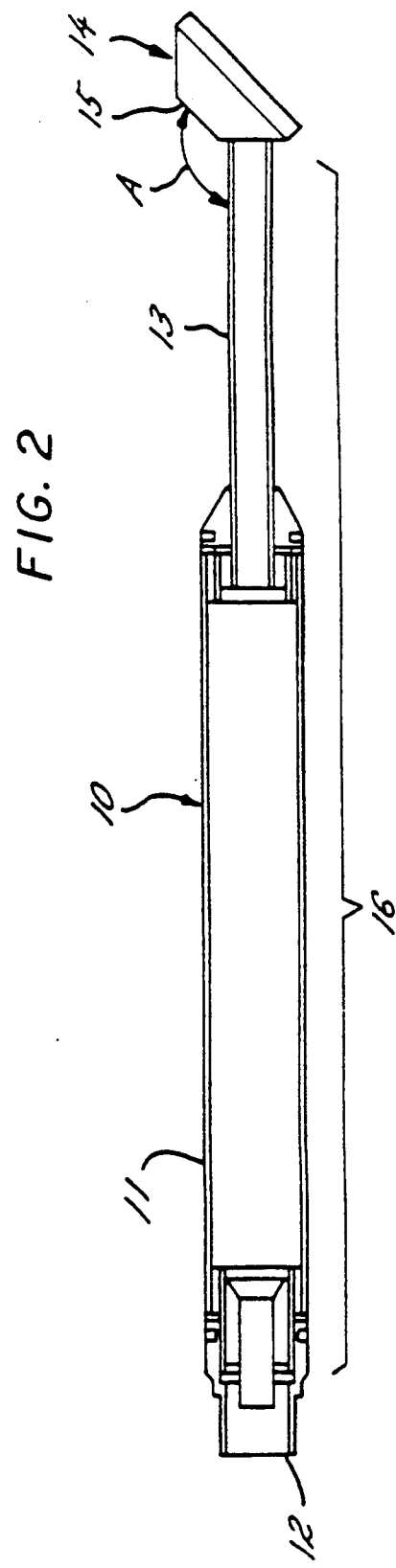
FIG. 2 is a cross sectional view of one embodiment of a video dental camera constructed in accordance with the teachings of this invention.

FIG. 2 shows a cross section of one embodiment of a video dental camera constructed in accordance with the teachings of this invention. Video dental camera 10 includes body 16 having handle 11 suitable for being held by an operator, and, if desired having forward extension 13. At one end of handle 11 is located connector 12 for connection, via a cable assembly (not shown) to video processor and control unit 8 (FIG. 1). If desired, forward extension 13 and handle 11 have generally circular cross section, although suitable shapes, such as octagonol, and polygonal can be used. The important point is that handle 11 should be easily and comfortably griped by the user, and forward extension 13 should be of a general size and cross section which is convenient for insertion into the patient's mouth and, of course, comfortable for the patient.

Located at the distal end of forward extension 13, and mounted on forward extension 13 at an angle A to forward extension 13, is camera head 14. Face 15 of camera head 14 includes means for receiving an image within a patient's mouth to be displayed on a video monitor. In one embodiment of this invention, such means for receiving the image is fiber optic tubes or one or more rod lens assemblies or a combination thereof with or without additional lenses, which transmit the image to an image sensor (not shown) either within forward extension 13, body 16 or, in another embodiment of this invention, the image is transmitted by one or more rod lens assemblies or fiber optic cable, or a combination thereof with or without additional lenses, through connector 12 to an image sensor located in external video equipment (not shown). However, in a preferred embodiment the image sensor is located directly in camera head 14 and receives the image from the patient's mouth via a lens, without the need for fiber optics.

Figure 3:
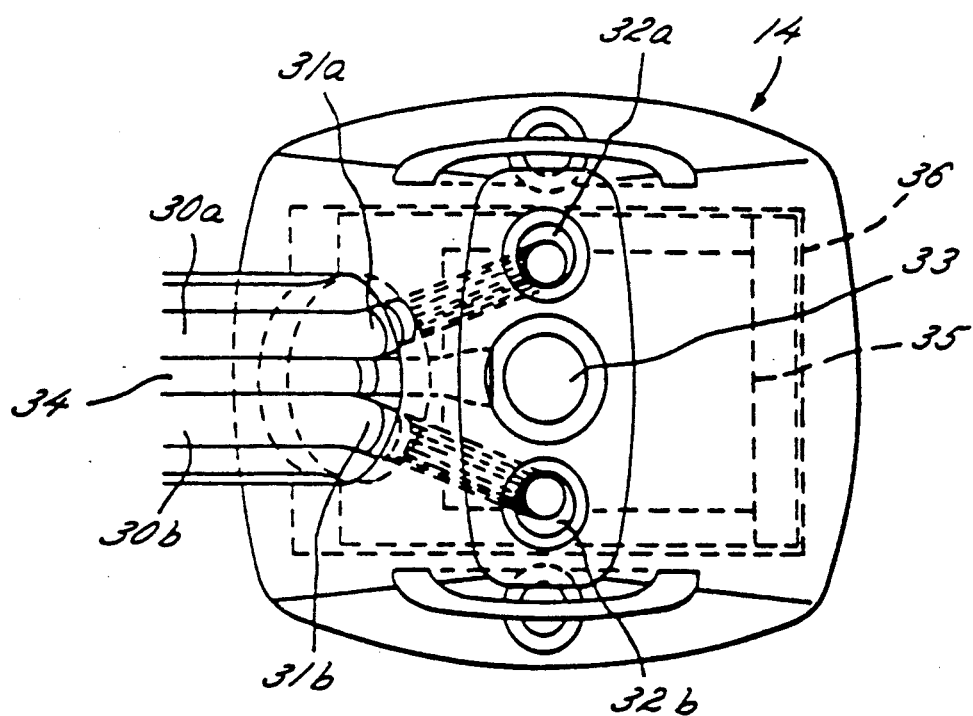
FIG. 3 is a plan view of one embodiment of a camera head constructed in accordance with the teachings of this invention.

FIG. 3 shows a cross sectional phantom view of camera head 14. In this embodiment, fiber optic light guides 30a and 30b are used to receive light from a light source (not shown) which may comprise, for example a halogen lamp or a Xenon arc lamp located at the proximal end of light guides 30a and 30b, and conduct this light through fiber optic curvatures 31a and 31b to illumination lenses 32a and 32b respectively. Also shown in FIG. 3 is image lens 33 and image sensor 35 which is mounted on hybrid assembly substrate 36 located within cavity 37. As shown in FIG. 3, in one embodiment of this invention, the center of the ends of fiber optic light pipes 30a and 30b are offset from the center of illumination lenses 32a and 32b, respectively, in a direction toward image lens 33. This causes the light being emitted from fiber optic light pipes 30a and 30b to be directed toward the image being viewed. Also, in one embodiment of this invention, illumination lenses 32a and 32b are dispersion lenses which include a "frosting" to disperse the light. Image sensor 35 is connected to video control cable 34 which communicates power and control signals to image sensor 35 and communicates video signals to the video processor and control means 8 of FIG. 1. As an alternative embodiment, a third fiber optic cable or a rod lens assembly (not shown) is used to conduct the image from image lens 33 to an image sensor located in forward extension 13, handle 11, or via connector 12 (FIG. to an image sensor located external to dental camera 10.

Figure 4:
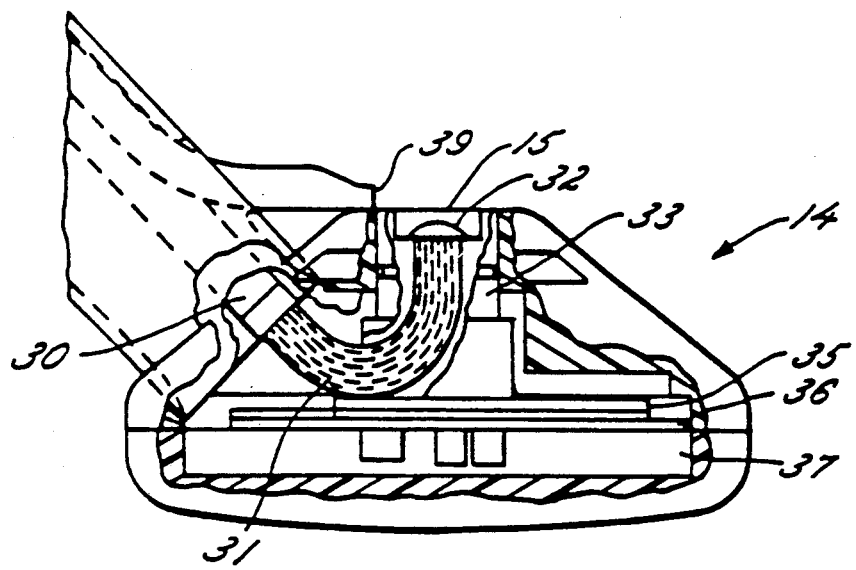
FIG. 4 is a cross sectional view of one embodiment of a camera head constructed in accordance with the teachings of this invention.

FIG. 4 shows a cross sectional phantom view of the structure shown in FIG. 3, with elements numbered in a similar fashion. Thus, shown in FIG. 4 are fiber optic light guide 30, fiber optic curvature 31, and illumination lens 32. In one embodiment, illumination lens 32 is a dispersion lens which serves to properly distribute the light over a wider angle and area upon exit from fiber optic light guide 30, to correspond to the field of view of image lens 33. FIG. 4 also shows image lens 33 located within camera head 14 between camera head face 15 and image sensor 35. In the embodiment shown in FIG. 4, image lens 33 is affixed directly to image sensor 35. In an alternative embodiment of this invention, image lens 33 is affixed to the body of camera head 14, and image sensor 35 is also affixed, via substrate 36, to the body of camera head 14, thereby maintaining image lens 33 and image device 35 in fixed relationship. In another embodiment of this invention, fiber optic curvature 31 is not used, but is replaced by a prism or mirror assembly which serves to reflect light from fiber optic light guide 30 to face 15 of camera head 14. If desired, a suitable lens can be placed on the fiber optic side of the prism or mirror, or on the face 15 side of the prism or mirror, or in both locations if desired.

In one embodiment of this invention an infrared filter is place between the light source (not shown) and fiber optic light guide 30. This infrared filter serves to prevent damage to fiber optic light guide 30 by masking out damaging infrared rays from the light source. In another embodiment of this invention, color filters are used as desired. For example, color filters can be placed anywhere between the light source and illumination lens 32 in order to selectively apply desired colors of illumination to the image being viewed. Alternatively, one or more color filters can be placed between image lens 33 and image sensor 35, again in order to selectively remove desired colors of the image being presented to image sensor 35. In yet another embodiment, an infrared blocking filter is placed in the image path between the image being viewed and image sensor 35 in order to prevent infrared energy from being applied to image sensor 35. This is particularly useful, for example, when a dentist is using a laser to perform certain dental procedures during which time a relatively larger amount of infrared energy is present. If not blocked out, this infrared energy would be detected by image sensor 35, resulting in a "washed out" video signal.

In one embodiment of this invention, forward extension 13 includes fluid jet 39 (FIG. 4) which serves to allow fluid to be introduce across face 15 of camera head 14. In this manner, for example, a constant or pulsed flow of gas, such as air, can be made to provide a laminar flow across image lens 33 to prevent fogging. If desired, a liquid such as water can be introduced as well in order to clean image lens 33. Fluid jet 39 can also be placed in any convenient location.

Figure 5:
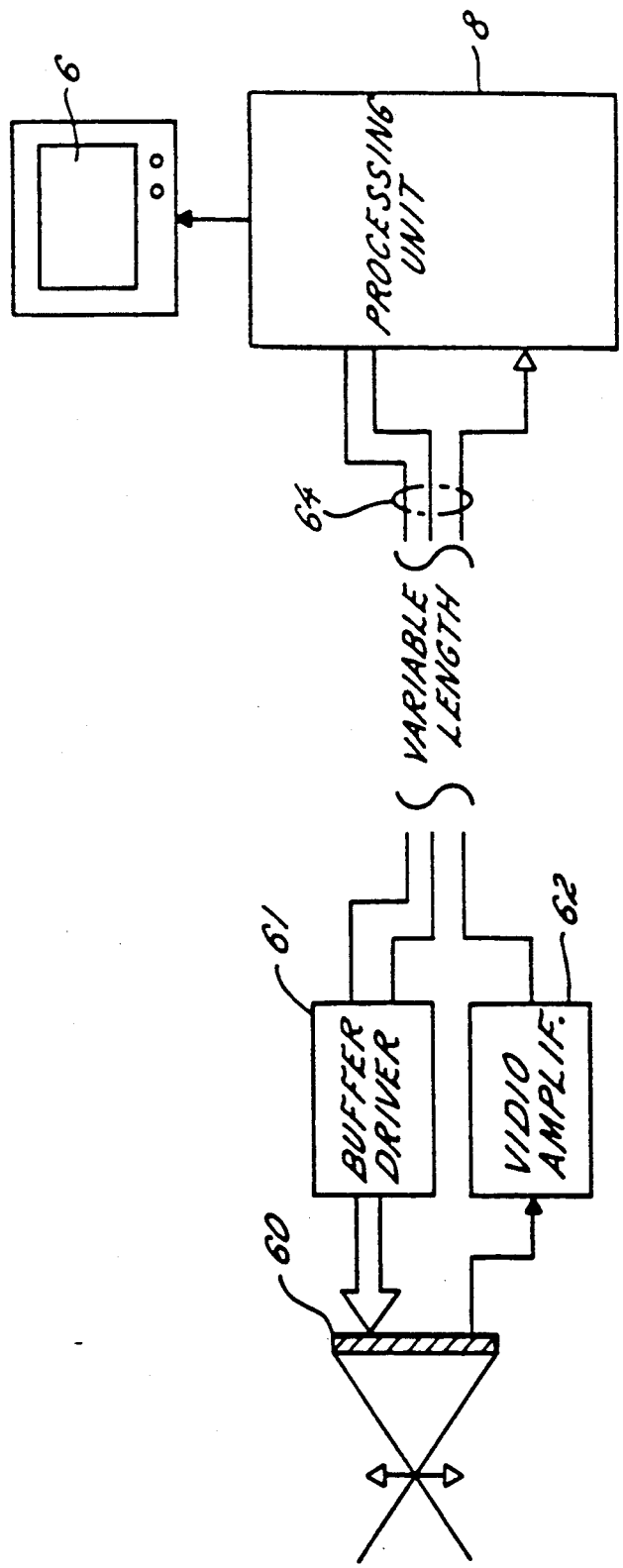
FIG. 5 is a block diagram depicting a dental camera system constructed in accordance with the teachings of this invention.

FIG. 5 is a block diagram of the electronics portion of a dental camera which includes image device 60 such as a charge coupled device (CCD), image device driver buffer 61 which serves to control image device 60, video amplifier circuitry 62, and video processor 8 for controlling driver buffer 61 and processing the video information which is then presented to display 6. For best results, driver buffer 61 and video amplifier 62 are located very close to image device 60 in order to maintain the necessary drive pulse waveforms and timing relationships, and insure the optimum frequency response of the video image. Ideally, these circuits are fabricated on the same integrated circuit as imaging device 60. Alternatively, driver buffer 61 and video amplifier 62 are formed as individual components in a hybrid or printed circuit board assembly with imaging device 60. However, in certain embodiments of this invention, this is not possible due to size limitations of the dental camera head 15 (FIG. 1. Also, the heat generated by driver buffer 61 and video amplifier 62 can, in certain instances, impair the operation of the imaging device 60, for example by raising the dark current.

In one embodiment of this invention, driver buffer 61 and video amplifier 62 are located as either individual circuits, a single integrated circuit, or a hybrid assembly, located in any convenient location within the dental camera. Such convenient locations are handle 11, forward extension 13, or within connecting cable 7 (FIG. 1).

Figure 6:
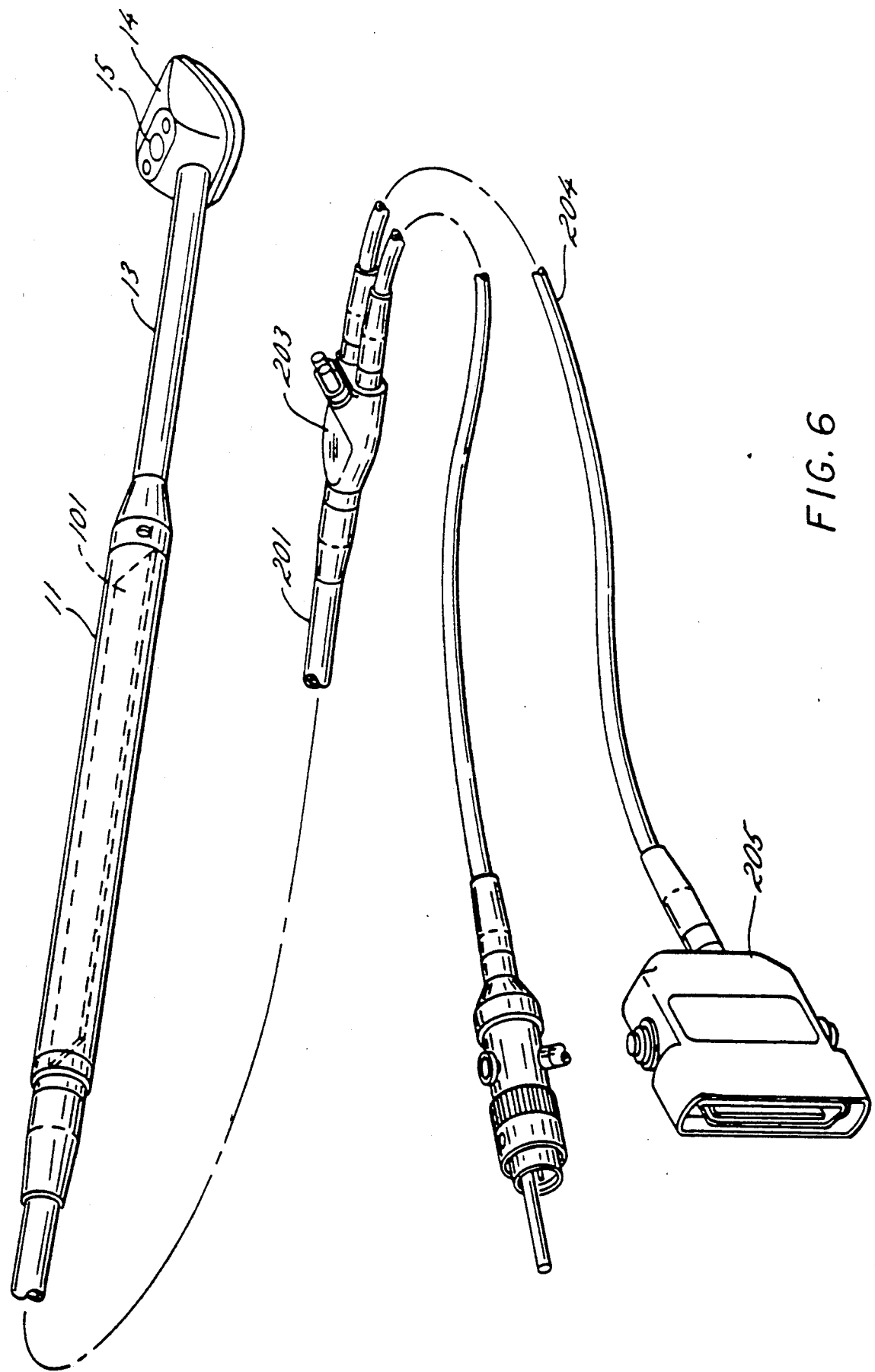
FIG. 6 is a diagram depicting a dental camera constructed in accordance with the teachings of this invention depicting where certain electronics may be conveniently located.

FIG. 6 is a drawing of one embodiment of a dental camera constructed in accordance with the teachings of this invention. As shown in FIG. 6, circuitry 101 may be included within handle 11. Circuitry 101 can include one or both driver buffer 61 and video amplifier 62 (FIG. 5), and can be formed either as an integrated circuit, hybrid device, or components located on a printed circuit board or the like. If desired, circuitry 101 includes an imaging device which receives visible light via, for example, a rod lense assembly or one or more optical fibers (not shown) which serve to transport the image from dental camera head 14 to circuitry 101.

In an alternative embodiment of this invention, electronics as described above may be located within cable 201, connector assembly 203, cable 204, connector 205, or within processing unit 8 (FIG. 5). Alternatively, various portions of the electronics can be conveniently located within a plurality of locations shown in FIG. 6.

Figure 7:
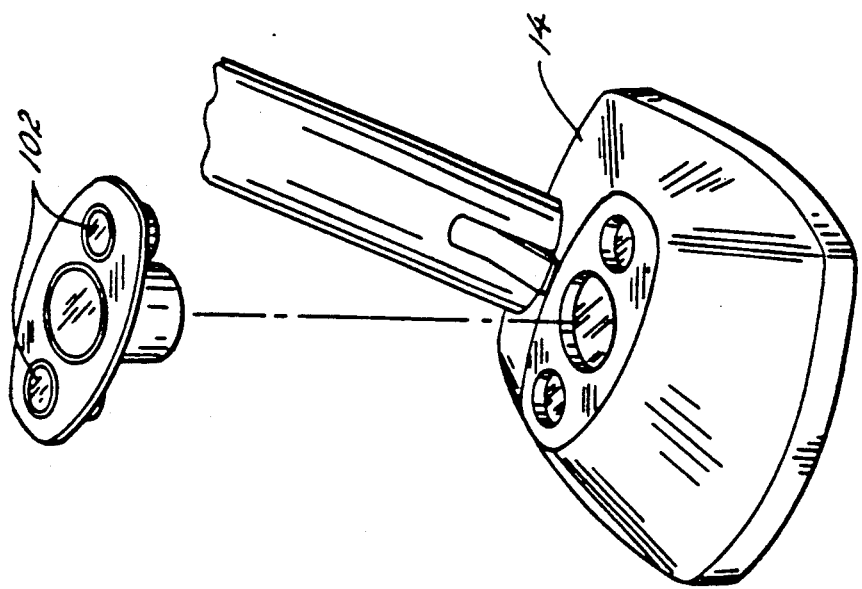
FIG. 7 depicts one embodiment of a dental camera constructed in accordance with the teachings of this invention which includes a dental camera head designed for receiving one of a plurality of attachments, such as the wide angle lens shown in FIG. 7.

FIG. 7 is a diagram of a dental camera constructed in accordance with the teachings of this invention which includes provisions in head 14 for mounting an external device. In one embodiment of this invention, a dental camera is provided which allows for such external devices to be removed and interchanged, thereby allowing a single dental camera to serve a wide of number of uses.

Figure 7B:
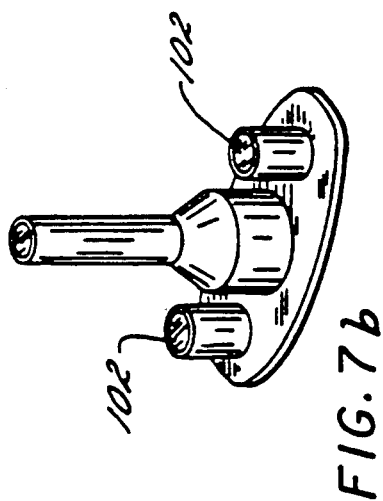
FIGS. 7a, 7b and 7c depict a telephoto lens, a relay lens, and an alternative embodiment of a relay lens, respectively, suitable for use with the dental camera head of FIG. 7.
Figure 7D:
FIG. 7d is a top view of the lens of FIG. 7c.
Figure 7A:
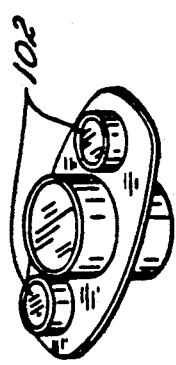
Figure 7C:
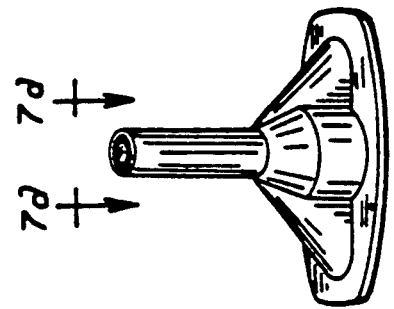

In accordance with the teachings of this invention, a number of possible external devices are provided, included but not limited to a wide angle lens as shown in FIG. 7, a telephoto lens as shown in FIG. 7a, a rod lens or one or more fiber optic cables serving as a "relay lens" as shown in FIG. 7b. Such a telephoto lens of FIG. 7a is very convenient for viewing very small areas, for example for use in viewing the capillaries within the gums, thereby allowing the dentist or oral surgeon to determine the relative health of the gums by determining the condition of blood circulation within the gums. Such a telephoto lens is also useful for obtaining a frontal view of the entire mouth, by holding the telephoto lens at an appropriate distance from the patient's face. Use of a telephoto lens for this purpose avoids the frontal image of the patient's mouth appearing as a "fish eye" view. A relay lens as in FIGS. 7b and 7c is highly suitable for viewing the small spaces between the teeth more readily than can be viewed using the dental camera itself. Each of these examples in FIGS. 7, 7a, and 7b include provisions for providing light to the area to be imaged. These take the form of additional lenses or windows 102 which optimize the area and uniformity of illumination to correspond to the angle of view of the lens being used. Alternatively, a relay lens as shown in FIG. 7c is provided, in which, for example, an optical fiber is used to both transmit light to the area to be imaged, and transmit the image to the dental camera imaging device contained within dental camera head 14. FIG. 7d is a top view of the lens structure of FIG. 7c. Filter attachments and lens/filter combinations can also be used. For example, infrared filters can be used to block infrared energy emitted by a laser during surgery, thereby allowing proper viewing of the surgery in process. Alternatively, color filters can be placed in the path of the light being emitted by the light source in order to selectively apply desired colors of illumination to the image being viewed. Alternatively, filters can be placed in the path of the light being received by the image device in order to selectively remove desired colors of the image being present to the image sensor.

Figure 8B:
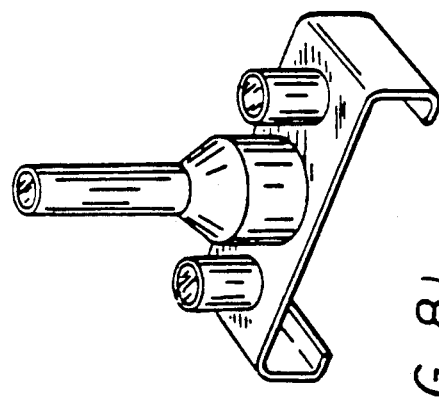
FIGS. 8a and 8b depict a telephoto lens, and a relay lens, respectively, suitable for use with the camera head of FIG. 8.
Figure 8:
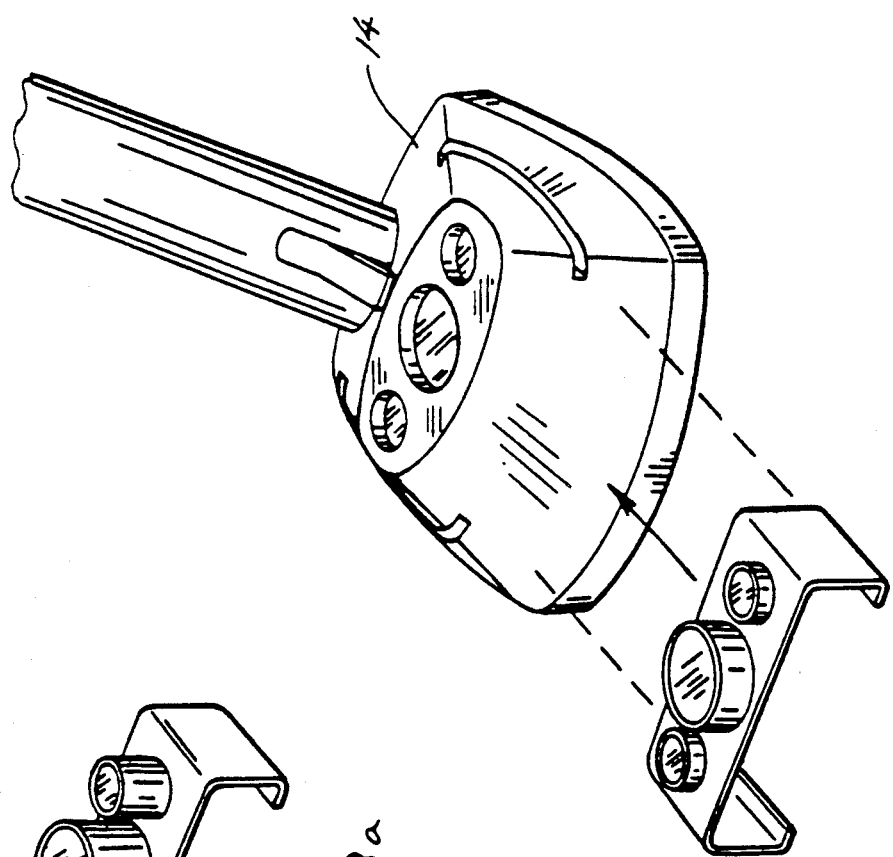
FIG. 8 is an alternative embodiment of a dental camera head constructed in accordance with the teachings of this invention which allows one of a plurality of attachments to be used, and a wide angle lens serving as such an attachment.
Figure 8A:
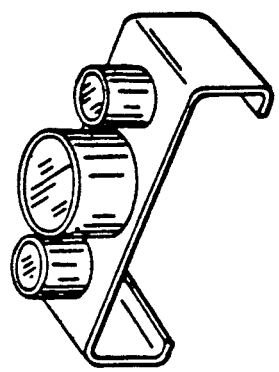

FIGS. 8, 8a, and 8b show alternative embodiments of the wide angle, telephoto, and relay lenses, respectively, which are capable of being clipped on to dental camera head 14 which includes slots 105 for reception of attachment bracket 106. Filters can also be used as described above with regard to FIG. 7.

FIGS. 9a through 9d depict various embodiments of a dental camera constructed in accordance with the teachings of this invention suitable for transillumination of an area to be examined. For example, in the embodiments of FIG. 9a and FIG. 9c, illumination means 30, such as an optical fiber, receives light from a light source within camera head 14 (or via means which carries light to camera head 14), and provides this light via, for example, optical fibers or a rod lens, to the opposite side of the area being examined, for example a tooth, thereby allowing the tooth to be transilluminated and the image provided to the dental camera head being that of the transilluminated tooth. Alternatively, this transillumination technique will allow the exterior of the tooth to be illuminated, and the interior of the tooth to be viewed, for example to view a cavity within the tooth, or the root canal. In one embodiment of this invention, illumination means 30 are malleable in order to allow their position with respect to camera head 14 to be altered, as desired.

Figure 9A:
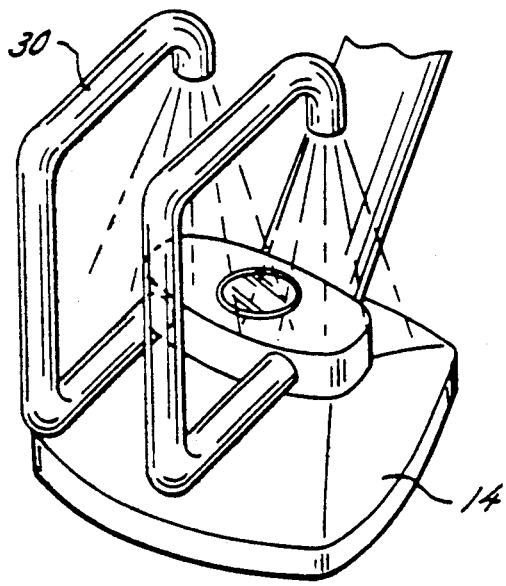
FIGS. 9a through 9f depict various embodiments of a transillumination device constructed in accordance with the teachings of this invention.
Figure 9B:
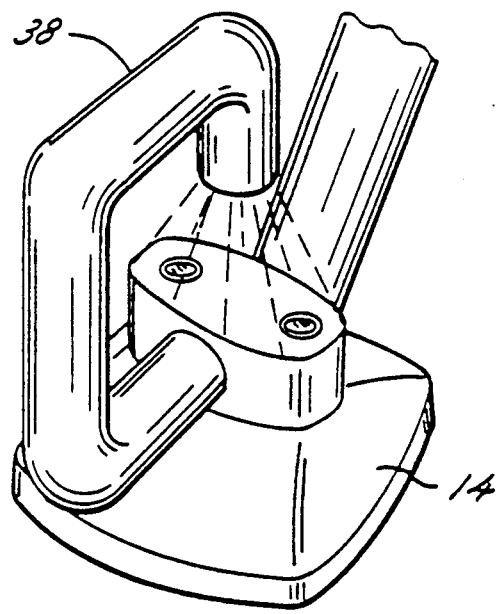
Figure 9C:
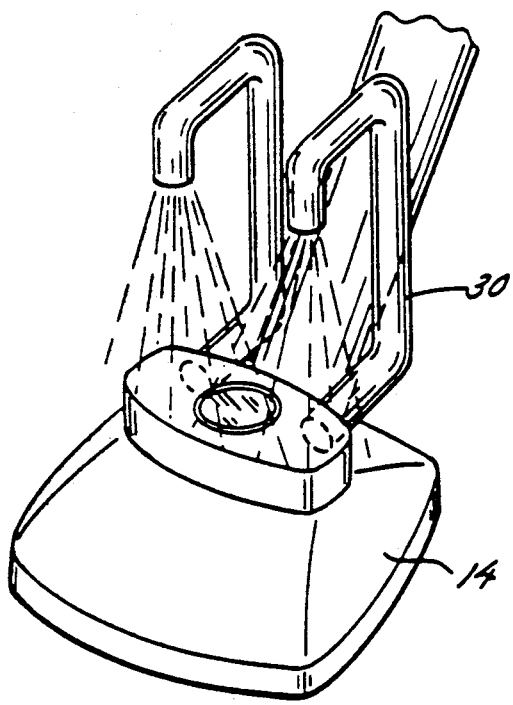
Figure 9D:
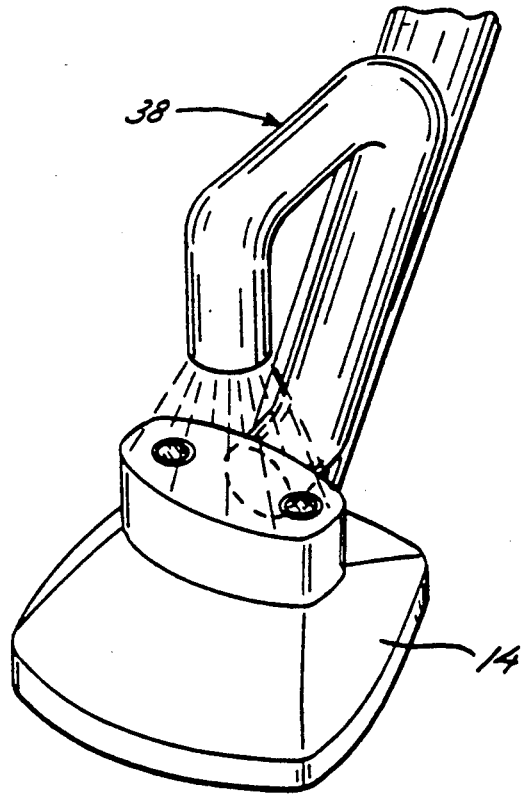

As shown in the embodiments of FIGS. 9b and 9d, light is emanated from camera head 14 for transillumination of an area to be viewed, and the transilluminated image is received by means 38, such as one or more optical fibers, or a rod lens, for transmission to the imaging device within the dental camera. In one embodiment of this invention, means 38 is malleable to allow its position relative to camera head 14 to be altered, as desired.

Figure 9F:
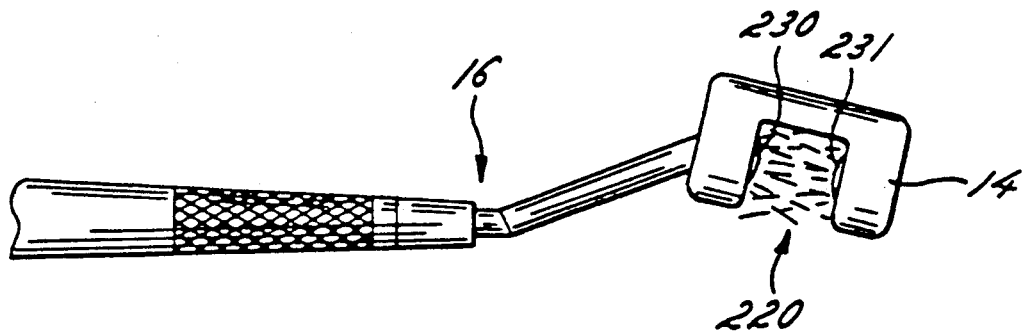
Figure 9E:
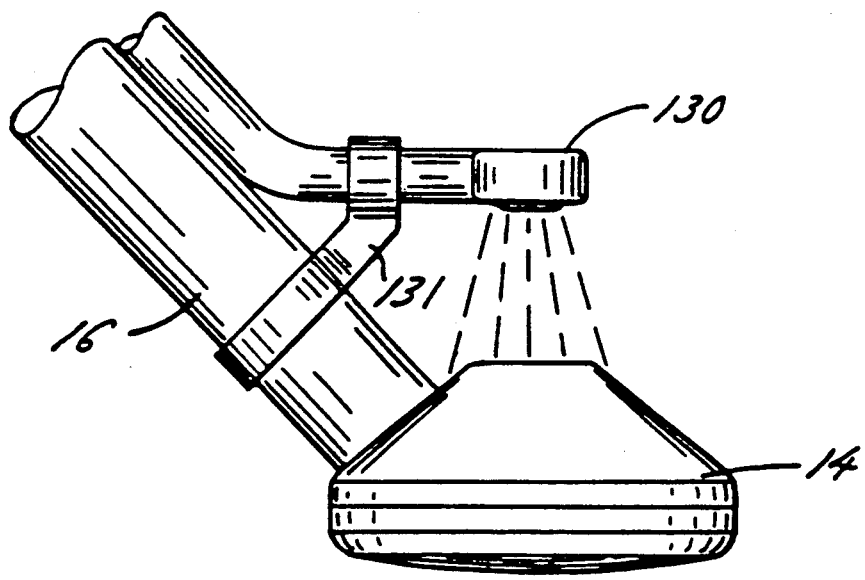

In an alternative embodiment of this invention, as shown in FIG. 9e, a separate transillumination light source 130 is used, which is attached to camera body 16 by attachment means 131. If desired, attachment 131 can allow the position of transillumination light source 130 to be changed relative to camera head 14. In this embodiment, camera head 14 either does not include light sources, or the light sources contained within camera head 14 are turned off during the use of transillumination light source 130.

FIG. 9f depicts an alternative embodiment of a transillumination device constructed in accordance with the teachings of this invention. As shown in FIG. 9f, camera head 14 includes a central cavity 220 which is placed in order to house the object to be transilluminated. On the interior walls of transillumination head 14 is included optical ports 230 and 231, either one of which may be the source of transillumination light, with the opposite optical port serving as the port for receiving the transilluminated image.

Figure 10:
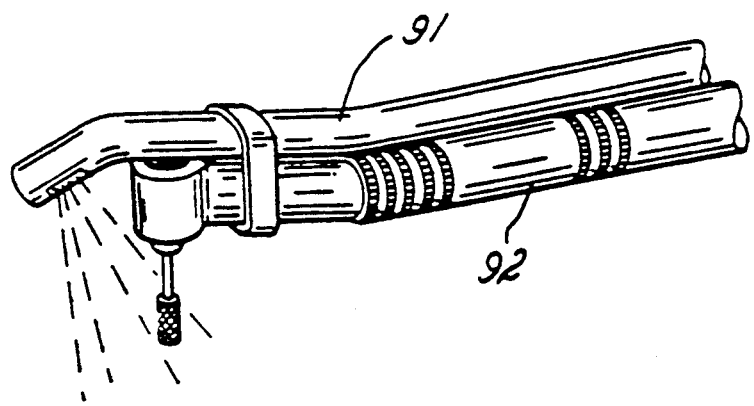
FIG. 10 depicts one embodiment of a dental camera constructed in accordance with the teachings of this invention and which is attached to a dental instrument.
Figure 11:
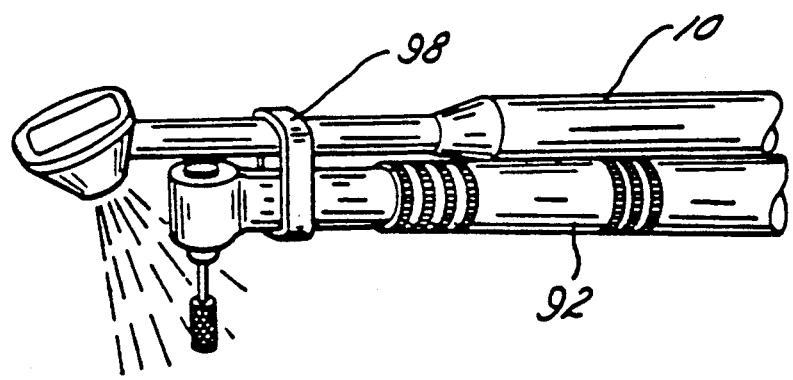
FIG. 11 is an alternative embodiment of a dental camera attached to a dental instrument.
Figure 12:
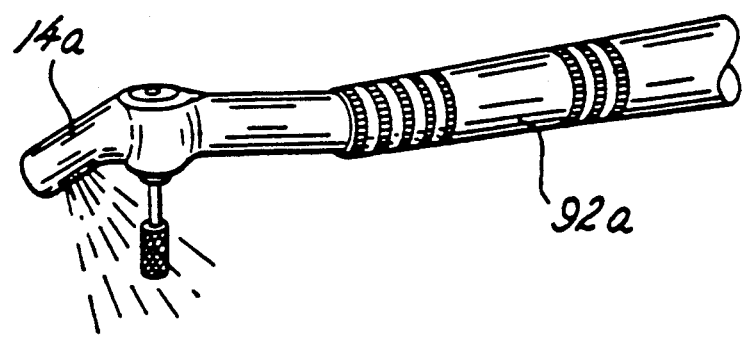
FIG. 12 is a view of one embodiment of a dental camera constructed in accordance with the teachings of this invention which is integrally formed with a dental instrument.

In another embodiment of this invention (FIG. 10), a rod lens or one or more optical fibers 91 are used for attaching the dental camera directly to a dentist's drill 92, thereby allowing the operation being performed by the dentist using his drill to be viewed on a video monitor. In an alternative embodiment shown in FIG. 11, a dental camera 10 is mounted to a dental drill 92, for example, by means of one or more clips or ties 98. In yet another embodiment of this invention, as shown in FIG. 12, the dental camera and dental drill are combined in a single instrument including camera head 14a attached to the end of dental drill/camera 92a. In one embodiment of this invention, camera head 14a includes an imaging device. In an alternative embodiment of this invention, camera head 14a includes means for receiving image, such as a fiber optic or a rod lens assembly, for transmission to an imaging device located within drill/camera 92a, or to the cable (not shown) or processor (not shown) attached to drill/camera 92a.

All publications and patent applications are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

What is claimed is:

1. A dental camera for use in displaying an image from inside the mouth onto a monitor comprising an electronic video endoscope comprising:
   a handle;
   a camera head at the distal end of said handle, including a transillumination device.

2. A dental camera as in claim 1 wherein said camera head includes an image device.

3. A dental camera as in claim 1 which further comprises a camera lens which is removably connected to said camera head.

4. A dental camera as in claim 3 wherein said camera lens is selected from the group of camera lenses consisting of wide angle, telephoto, and relay lenses.

5. A dental camera as in claim 1 wherein said transillumination device comprises means for illuminating the exterior of a tooth and means for receiving an image from within said tooth.

6. A dental camera as in claim 5 wherein said means for receiving an image is selected from the group of mirrors, lenses, optical fibers, and filters.

7. A dental camera as in claim 5 wherein said means for providing light comprises a rod lens or an optical fiber.

8. A dental camera as in claim 5 wherein said means for providing light is malleable.

9. A dental camera as in claim 1 wherein said transillumination device comprises means for receiving an image and means for providing light to the opposite side of the object being viewed.

10. A dental camera as in claim 9 wherein said means for receiving an image is selected from the group of mirrors, lenses, optical fibers, and filters.

11. A dental camera as in claim 9 wherein said means for providing light comprises a rod lens or an optical fiber.

12. A dental camera as in claim 9 wherein said means for providing light is malleable.

13. A dental camera as in claim 9 which further comprises a filter located in the path of said received image.

14. A dental camera as in claim 13 wherein said filter is located between said means for receiving an image and said image device.

15. A dental camera as in claim 13 wherein said filter is an infrared filter.

16. A dental camera as in claim 13 which further comprises a filter in the path of the light from said light source.

* * * * *